(12) United States Patent
Li

(10) Patent No.: US 7,542,542 B2
(45) Date of Patent: Jun. 2, 2009

(54) X-RAY COMPUTED TOMOGRAPHY APPARATUS

(75) Inventor: Qinglei Li, Beijing (CN)

(73) Assignee: GE Medical Systems Global Technology Company, LLC, Waukesha, WI (US)

( * ) Notice: Subject to any disclaimer, the term of this patent is extended or adjusted under 35 U.S.C. 154(b) by 0 days.

(21) Appl. No.: 11/829,504

(22) Filed: Jul. 27, 2007

(65) Prior Publication Data

US 2008/0025460 A1    Jan. 31, 2008

(30) Foreign Application Priority Data

Jul. 28, 2006    (CN) .................. 2006 1 0121230

(51) Int. Cl.
*G01N 23/00* (2006.01)
(52) U.S. Cl. .................. 378/15; 378/4; 378/205
(58) Field of Classification Search .............. 378/4, 378/15, 193–198, 204, 205; 73/458; 700/279
See application file for complete search history.

(56) References Cited

U.S. PATENT DOCUMENTS

| | | | |
|---|---|---|---|
| 5,448,608 A | 9/1995 | Swain et al. | |
| 6,550,317 B2 | 4/2003 | Steinlage et al. | |
| 6,748,806 B2 | 6/2004 | Halsmer | |
| 6,890,100 B2 | 5/2005 | Reznicek et al. | |
| 7,236,855 B2 | 6/2007 | Danz et al. | |
| 2007/0041488 A1* | 2/2007 | Hoheisel et al. ................. | 378/4 |

* cited by examiner

*Primary Examiner*—Jurie Yun
(74) *Attorney, Agent, or Firm*—Armstrong Teasdale LLP

(57) ABSTRACT

A computed tomography apparatus is capable of adjusting rotational balance of gantry rotating part in a wide range with easy control. A computed tomography apparatus 100 comprises a rotating part 130 having an X-ray tube 102, a rotating part 130 having an X-ray detector for detecting X-rays from the X-ray tube, at least two mass bodies (M1, M2) provided at the rotating part, movable in the direction of circumference, a driving part 72 for moving at least two mass bodies, a sensor (S) for measuring the vibration of the rotating part and a controller 137 for controlling the driving part for driving the mass bodies on a basis of the outputs of the sensor.

9 Claims, 7 Drawing Sheets

X-RAY COMPUTED TOMOGRAPHY APPARATUS

CROSS REFERENCE TO RELATED APPLICATIONS

This application claims the benefit of Chinese Application No. 200610121230.9 filed Jul. 28, 2006.

BACKGROUND OF THE INVENTION

The present invention relates to an X-ray CT (Computed Tomography) apparatus that irradiates with X-rays around a patient who is a subject to be examined and that processes obtained projection data to create tomographic images of the subject, and more particularly relates to an X-ray computed tomography that improves balance of a gantry rotating part.

An X-ray computed tomography apparatus comprises an X-ray tube and multiple-row X-ray detector at a gantry rotating part. Unbalance of the gantry rotating part may cause vibration during rotation of the gantry rotating part, which largely affects image qualities. Therefore, rotational balance of the gantry rotating part is adjusted during manufacture of gantry and during replacement of components (e.g., an X-ray tube or a multiple-row X-ray detector).

There are demands for rotating the gantry rotating part at higher speed to reduce the time to examine the subject to be examined. Centrifugal force acting on the gantry rotating part is proportional to square of rotational speed of (angular speed) the gantry rotating part. For example, as the rotational speed of the gantry rotating part is made twice, the centrifugal force becomes four times. Accordingly, in order to suppress the vibration to the current level, unbalance of the gantry rotating part needs to be made one forth or rigidity of the gantry rotating part needs to be made four times larger than the current one.

Since increasing the rigidity of the gantry rotating parts makes the apparatus larger and increases its cost, it is preferable to make the unbalance of the gantry rotating part small. Methods disclosed, e.g., in U.S. Pat. No. 6,550,317 and U.S. Pat. No. 6,748,806 are applied for methods for adjusting the rotational balance of the gantry rotating part.

The invention of the patent document 1 is a method for adjusting static rational balance of the gantry rotating part. However, the method disclosed in the patent document 1 requires repetition of the arrangement of small mass body (hereinafter may be called a mass), which makes the operation time longer. Moreover, this method cannot be applied for variation of dynamic rotational balance.

The invention of the patent document 2 is a method for adjusting dynamic rotational balance in that at least two masses are moved from the center of the gantry rotating part towards the radial directions. This invention solves the problem of the patent document 1. However, the method disclosed in the patent document 2 can adjust the rotational balance only in a small range with two masses. In order to adjust the rotational balance in a wide range, it requires three or more masses, which also requires the complicated control.

SUMMARY OF THE INVENTION

The present invention is to provide an X-ray computed tomography apparatus which can adjust the rotational balance of the gantry rotating part in a wide range with simplified control.

The first aspect of the X-ray computed tomography apparatus comprises a rotating part having an X-ray tube and an X-ray detector for detecting X-rays from the X-ray tube, at least two mass bodies provided at the rotating part and movable in a direction of circumference, a driving part for moving at least two mass bodies, a sensor for measuring vibration of the rotating part, and a controller for controlling the driving part to move at least two mass bodies on a basis of outputs of the sensor.

According to this configuration, the mass body can be moved so that the eccentricity of the center of mass becomes less. In the U.S. Pat. No. 6,748,806 publication, the mass bodies are moved from the center of the gantry rotating part towards the radial directions. Comparing a case of a mass body to be moved by a certain distance towards the radial directions with a case of a mass body to be moved by a certain distance in the direction of circumference, arranged in the same radius, the case of the mass body to be moved in the direction of circumference can make the eccentricity of the center of mass 1.41 times. This means that small mass body can make the center of mass eccentric.

According to the second aspect of the X-ray computed tomography apparatus, a radius that the mass body moves in the direction of circumference is a first radius and a second radius different from the first radius.

The mass bodies are provided at the first radius and the second radius each having the different radius, respectively, so that in a case of fine adjustment, the mass body at the smaller radius is moved while in a case of coarse adjustment, the mass body at the larger radius is moved. Therefore, the fine adjustment and coarse adjustment can easily be performed.

According to the third aspect of the X-ray computed tomography apparatus, when the X-ray tube and/or the X-ray detector is installed at the rotating part, base position of at least two mass bodies is determined.

When the X-ray tube or other component is installed at the rotating part, the base position of the mass body is determined by calculating the weight of the X-ray tube or other component so that the center of mass is made near the center of rotation. Thereafter, the rotating part is rotated and the vibration of the rotating part is measured by the sensor. Accordingly, the rotating part does not resonate so that the X-ray computed tomography apparatus is not damaged.

According to the fourth aspect of the controller, when it determines that the rotating part is in the condition of mechanical resonance on a basis of the outputs of the sensor, the mass body is moved by a predetermined distance without calculating the travel amount of the mass body.

Continuous resonance of the rotating part makes the possibility of causing damages to the X-ray computed tomography apparatus including the rotating part higher. Therefore, in order to escape from the resonance rapidly, as soon as it is determined that the resonance occurs, the mass body is rapidly moved by a predetermined distance without calculating the travel amount of the mass body. Accordingly, the rotating part does not resonate so that the X-ray computed tomography apparatus is not damaged.

According to the fifth aspect of the controller, it calculates the travel amount of the mass body on a basis of the outputs of the sensor, and the mass body is moved by the calculated travel amount by the driving part.

As the mass body is moved by the calculated travel amount, the eccentricity of the center of mass is made near the center of rotation, which is within allowable range. Therefore, even though the rotational speed becomes higher, the vibration is kept low.

The sixth aspect of the X-ray computed tomography apparatus comprises two supports for supporting the rotating part.

The sensor includes a first sensor for detecting vibration in a first direction and a second sensor for detecting vibration in a second direction perpendicular to the first direction. The first sensor and the second sensor are provided to two supports, respectively.

The detection of the vibration differs largely depending on the arrangement of the sensor for measuring the vibration of the rotating part. In this aspect, the first sensor is attached to one support to detect the vibration in the first direction while the second sensor is attached to the other support to detect the vibration in the second direction. Accordingly, the eccentricity of the center of mass can easily be calculated.

According to the seventh aspect of the X-ray computed tomography apparatus, the mass body is moved as a movable piece of a linear motor equipment with respect to a stator.

The linear motor equipment is superior in response, and a permanent magnet or a coil constituting the movable body can be used as the mass body. Accordingly, it is suitable for the mass body to reduce the eccentricity of the center of mass.

According to the eighth aspect of the X-ray computed tomography apparatus, at least two mass bodies have different weight.

The weight of the mass bodies is different, so that in a case of fine adjustment, the light mass body is moved while in a case of coarse adjustment, the heavy mass body is moved. Therefore, the fine adjustment and coarse adjustment can easily be performed.

The X-ray computed tomography apparatus of the present invention has advantages that the rotational balance can be adjusted in the wide range by moving the mass in the direction of circumference and that the eccentricity of the center of mass can be made small with simplified control. Especially, the radiuses which the mass bodies are moved in the direction of circumference and the weight of plural mass bodies are made different, so that the fine adjustment and coarse adjustment can readily be performed.

BRIEF DESCRIPTION OF THE DRAWINGS

The above aspects, other advantages and further features of the present invention will become readily apparent from the following description of illustrative, non-limiting embodiments with reference to accompanying drawings, in which.

DETAILED DESCRIPTION OF THE PREFERRED EMBODIMENTS

<General Arrangement of X-Ray CT Apparatus>

Figure 1:
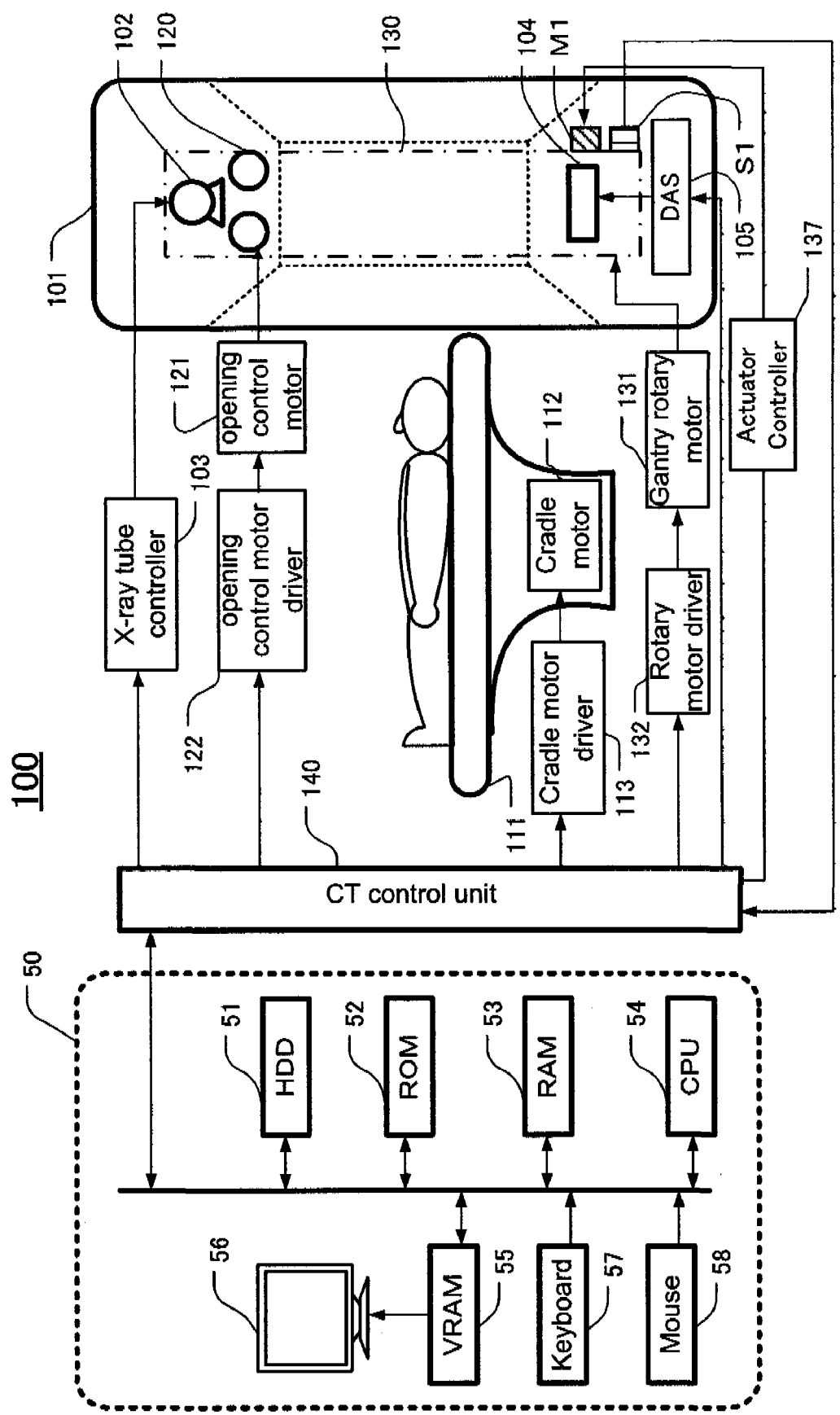
FIG. 1 is a block diagram showing the structure of an X-ray CT apparatus 100.

FIG. 1 is a perspective view showing a general arrangement of an X-ray CT apparatus 100. This apparatus generally includes a cradle 111 laying an examinee's body thereon, a gantry 101 irradiating X-rays to the examinee's body and acquiring X-ray transmitted through the examinee's body, and an operation console 50 adapted to display an X-ray radiographic image based upon data transmitted from the gantry 101.

The gantry 101 are communicatively coupled with a CT control unit 140 and various other devices which will be described later, and are configured to operate under control of the CT control unit 140.

Inside the gantry 101 are provided an X-ray tube 102 for producing X-rays, an X-ray tube controller 103 connected with the X-ray tube 102, a the collimator 120 having an opening for limiting a range of irradiation of X-rays, a opening control motor 121 for regulating a dimension of an opening (slit or aperture) of the collimator 120, and an opening control motor driver 122 for driving opening control motor 121. X rays that have passed through the collimator 120 form a cone-shaped beam of X rays (so-called "cone beam") following to the rotation direction of gantry 101 with the limitation of the range of irradiation of X-rays. The examinee's body is moved, laid on the cradle 111 in a decubitus position, to an axis of body, i.e. a Z-axis direction, by a cradle motor 112. This cradle motor 112 is driven by a cradle motor driver 113.

Also provided inside the gantry 101 is a multi-row X-ray detection unit 104, which includes multiple rows of detection channels each having a plurality of detectors. Each detector has a length depending upon a fan angle (normally 60° or so). The detection channels are arranged in a direction (element direction) along the Z-axis direction. The multi-row X-ray detection unit 104 is, for example, made up of a scintillator and a photodiode used in combination.

The gantry 101 includes at least one data acquisition unit or DAS (standing for Data Acquisition System) 105 which acquires projection data from outputs of the detection channels. The number of the data acquisition unit(s) 105 may be one or more (e.g., four, eight, sixteen or thirty two), and each data acquisition unit 105 is connected with the X-ray detection unit 104. For example, the gantry 101 including four data acquisition units 105, which is normally called "4DAS", includes the detection channels arranged in four rows in the element direction, and can obtain four slice images in one cycle of revolution of the X-ray tube 102. The X-ray tube 102 and the X-ray detection unit 104 are disposed in opposite positions in the gantry 101 such that a hollow space for accommodating an examinee's body is left between the X-ray tube 102 and the X-ray detection unit 104.

The X-ray tube 102 and the X-ray detection unit 104 are attached to a gantry rotating part 130 so that the X-ray tube 102 and the X-ray detection unit 104 revolve around the examinee's body while maintaining the opposed positions relative to each other. A gantry rotary motor 131 and a gantry rotary motor driver 132 are connected with the gantry rotating part 130, and the gantry rotating part 130 is regulated by the gantry rotary motor driver 132 to make one rotation in about 0.3 second to about 1.0 second. Sensors S are attached at an area around the gantry rotating part 130, they detects vibration of the gantry rotating part 130. Actuators M arranged in the gantry rotating part 130 are actuated by an actuator controller 137.

The CT control unit 140 is communicatively coupled with the operation console 50. Responsive to instructions from the operation console 50, various control signals are transmitted to the X-ray tube controller 103, the cradle motor driver 113 opening control motor driver 122, the rotary motor driver 132, the actuator controller 137 and the DAS 105. Data acquired by the data acquisition unit 135 are transmitted to the operation console 50 in which images are reconstructed and cross-sectional images are displayed.

The X-ray CT apparatus 100 provides user-selectable options of operation modes: a full-scan mode in which images are reconstructed from projection data of 360° and a half-scan mode in which images are reconstructed from projection data of 180° plus one unit fan angle.

The operation console 50 is typically embodied in a workstation, as illustrated in FIG. 1, which mainly includes a ROM 52 storing a boot program and the like, a RAM 53 serving as a main memory and a CPU 54 executing instructions for controlling the entire apparatus.

A hard disk drive or HDD 51 is provided in the operation console 50 to store not only an operating system but also image-processing programs for providing various instructions given to the gantry 101 and for reconstructing and displaying X-ray cross sectional images based upon data received from the gantry 101. A VRAM 55 is a memory in which image data to be displayed are deployed, that is, the image data, etc. can be deployed in the VRAM 55 and thereby displayed in a monitor 56. Operators use a keyboard 57 and a mouse 58 to perform a variety of operations and manipulations.

<Structure of the Inside of the Gantry 101>

Figure 2:
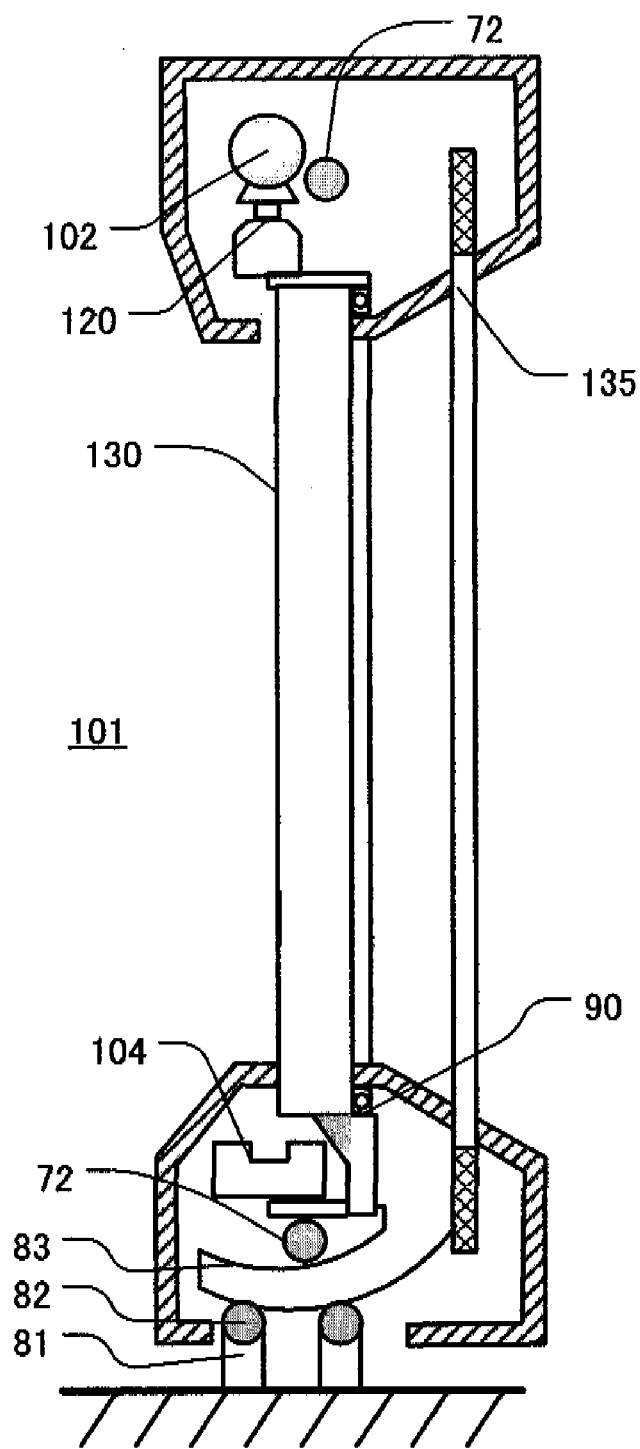
FIG. 2 is an enlarged sectional view of the inside of the gantry 101.

FIG. 2 is an enlarged sectional view of the inside of the gantry 101. There provided a rotational ball 82 on a base 81 placed on a floor. A sub-base 83 to be inclined fore and aft is provided on the rotational ball 82. A rotational motor 131 (see FIG. 1) is provided in the gantry 101, and a gantry rotating part 130 can rotate over a bearing 90. Rotation of the rotational motor 131 is transmitted to the gantry rotating part 130 through a belt which is not shown in figures and thus thereby the gantry rotating part 130 rotates. The gantry rotating part 130 includes a rail 72 that is a stator of a linear motor equipment, a self-propelled counter load M (see FIG. 3) that is a movable piece of the linear motor equipment as a mass body, an X-ray tube 102, a collimator 120 and an X-ray detection unit 104 therein.

The gantry rotating part 130 further has a slip ring 135 acing as a rotating electrode attached thereto. The slip ring 135 is a circular electric conductor in that a plurality of rings each having a different diameter are concentrically attached. The slip ring 135 is pressed to make contact with a brush of a plate spring acing as a stationary electrode which is an electric conductor, owing to the elasticity of the spring. Accordingly, power is supplied to the linear motor equipment, the X-ray tube 102, an opening control motor 121 or other components included in the gantry rotating part 130. Further, an X-ray detecting signal from the X-ray detection unit 104 is transmitted to the CT control unit 140 over the slip ring 135.

<Balance Adjustment of the Gantry Rotating Part 130>

First Embodiment

Figure 3:
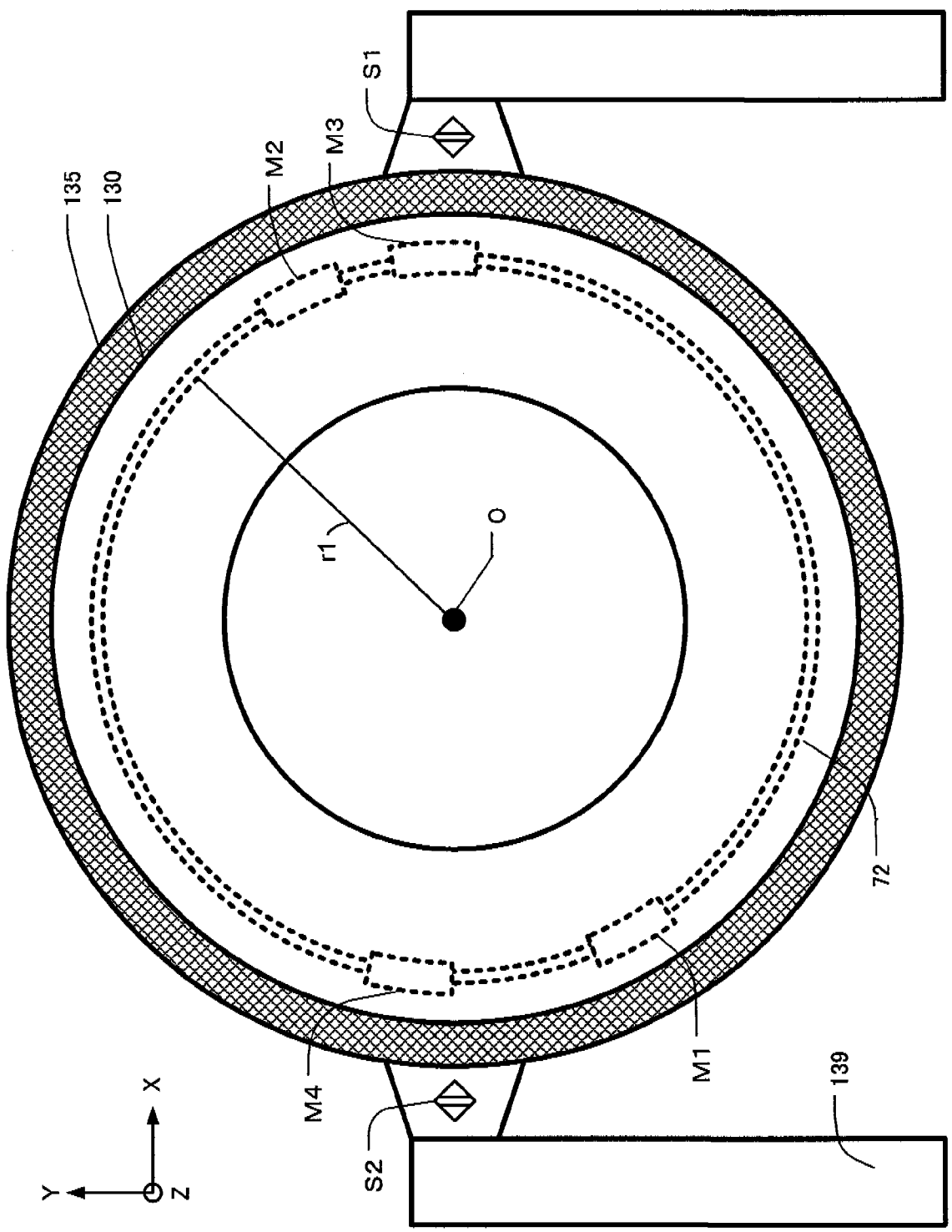
FIG. 3 is a schematic view showing the first embodiment of the gantry rotating part 130 of the X-ray CT apparatus 100 in X-Y plane.

FIG. 3 is a schematic view of the first embodiment showing the gantry rotating part 130 of the X-ray CT apparatus 100 in X-Y plane. The X-ray tube 102 and other components are not shown in FIG. 3. The circular ring rail 72 having a radius r1 the center of which is the center of rotation O of the gantry rotating part 130 is attached to the gantry rotating part 130. The self-propelled counter loads M1, M2, M3, M4 are attached along the ring rail 72.

The ring rail 72 and the self-propelled counter loads M1-M4 constitute a linear motor equipment. A plurality of coils which can switch N-pole and S-pole with the current flow are arranged along the circumference of the ring rail 72, that is, the ring rail 72 is a stator of the linear motor equipment. For the self-propelled counter loads M1-M4, a permanent magnet the N-pole of which faces to the coil and a permanent magnet the S-pole of which faces to the coil are arranged alternately, that is, the self-propelled counter loads M1-M4 are movable pieces of the linear motor equipment. Then, switching the current flow of the coil generates the magnetic field (N-pole and S-pole), so that the self-propelled counter loads M1-M4 are moved at a predetermined speed in a predetermined direction due to the magnetic repulsion and attraction of the permanent magnets of the self-propelled counter loads M1-M4. It does not require providing the mass to the self-propelled counter loads M1-M4 but requires only self-weight of permanent magnets.

The permanent magnet the N-pole of which faces to the self-propelled counter loads M1-M4 and the permanent magnet the S-pole of which faces to the self-propelled counter loads M1-M4 may be placed alternately at the ring rail 72, and a plurality of coils capable of switching N-pole and S-pole may be arranged to the self-propelled counter loads M1-M4. In this case, wiring for supplying power to the coils is complicated. It does not require providing weights to the self-propelled counter loads M1-M4 but requires only self-weight of coils.

An acceleration sensor S1 and an acceleration sensor S2 which both detect the vibration of the gantry rotating part 130 are installed at supports 139 for supporting the gantry rotating part 130. The acceleration sensor S1 detects the displacement, e.g., in an X-axis direction while the acceleration sensor S2 detects the displacement, e.g., in a Y-axis direction. Static or gyro sensors can be applied for the acceleration sensor S1 or S2. The acceleration sensor may be replaced with a displacement sensor such as a non-contact type displacement gauge, e.g., a laser displacement meter, or a distortion sensor for measuring expansion and contraction.

Figure 4:
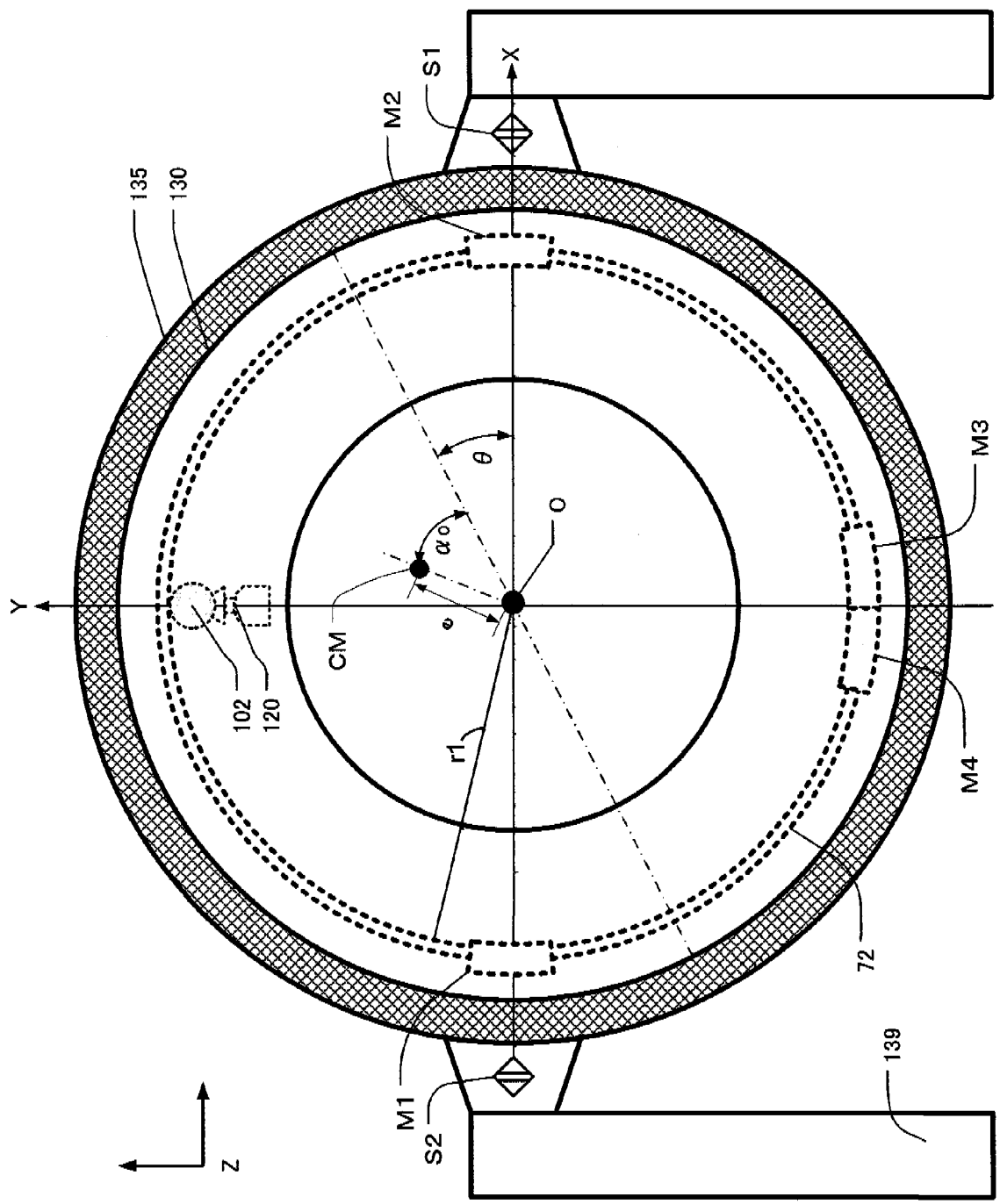
FIG. 4 is an explanatory view showing a method for adjusting the rotational balance of the gantry rotating part 130.

FIG. 4 is an explanatory view showing a method for adjusting the rotational balance of the gantry rotating part 130. As shown in FIG. 4, first, the self-propelled counter loads M3 and M4 are moved at the location symmetric to the X-ray tube with respect to the center of rotation O. This is because normally the center of mass of the gantry rotating part 130 is eccentric towards the X-ray tube 102 due to heavy weight acting on the portion on which the X-ray tube 102 and the collimator 120 are placed. Further, the self-propelled counter load M1 and M2 are arranged in the position where +90 degrees from the position of the X-ray tube 102 and −90 degrees from the position of the X-ray tube 102, respectively. In FIG. 4, according to the design, the eccentricity of the center of mass due to the X-ray tube 102 and the collimator 120 is corrected when the self-propelled loads M3 and M4 are moved to the locations where they are symmetric to the X-ray tube with respect to the center of rotation O. If which direction and how much the center of mass is eccentric from the center of rotation O can be obtained during designing, the self-propelled counter loads M1-M4 can be moved in accordance with the design.

The acceleration sensor S1 detects acceleration in an X-axis direction while the acceleration sensor S2 detects acceleration in a Y-axis direction. Then, the following equation is obtained.

$$\mathrm{Acc}(S1) = K_1 * e * \omega^2 * \cos(\alpha_0 + \theta)$$

$$\mathrm{Acc}(S2) = K_2 * e * \omega^2 * \sin(\alpha_0 + \theta)$$

$$\theta = \omega * t$$

Here, $K_1$ and $K_2$ are transfer coefficients less than one, which are unknown values and which are determined by the ratio of weight of the rotating member, tilt member, bearing and others.

e is a distance from the center of rotation O to the center of mass CM, which is an unknown value.

$\alpha_O$ is an angle made by the position of the gantry rotating part 130 and the center of mass CM, that is an unknown value.

θ is an angle made by an axis connecting the acceleration sensors S1, S2 (in FIG. 4, it is the X-axis) and the gantry rotating part 130, which is known.

ω is an angle velocity, which is known.

Outputs of the acceleration sensors S1, S2 are sensed at the sample time $T_1, T_2 \ldots T_n$, and applied to the above equations to obtain the unknown values. The average value of e and $\alpha_O$ is obtained from the outputs of the acceleration sensors S1, S2 per sample time. Accordingly, the eccentric position of center of mass CM of the gantry rotating part 103 can be determined.

<Operation of Balance Adjustment>

Figure 5:
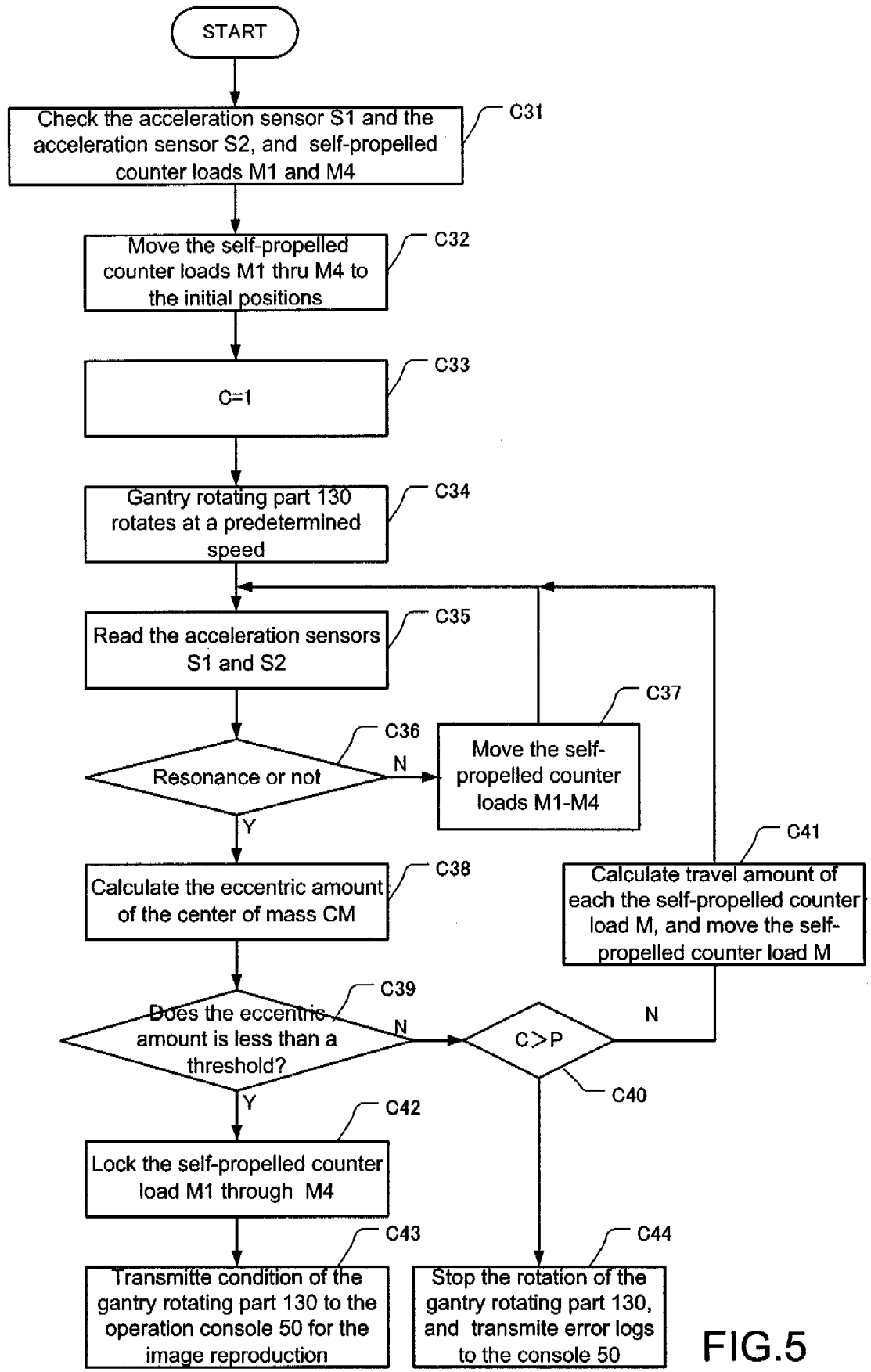
FIG. 5 is a flowchart showing the summary of the operation of the balance adjustment.

Next, the operation of the balance adjustment will be explained using a flowchart shown in FIG. 5.

In Step C31, first, checking whether the acceleration sensor S1 and the acceleration sensor S2 have any failure is performed. Moreover, checking whether the self-propelled counter loads M1 through M4 is capable of moving is performed.

In Step C32, the self-propelled counter loads M1 through M4 are moved to the initial positions. The initial positions, as described in FIG. 4, are the locations where the self-propelled counter loads M3 and M4 are placed symmetric to the X-ray tube 102 with respect to the center of rotation O.

In Step C33, the number of operation is initialized to C=1 in order to check the number of operations of travel amount of the self-propelled counter loads M1-M4.

In Step C34, the gantry rotating part 130 rotates at a predetermined speed with the rotational motor 131. As the rotational speed becomes faster, the acceleration sensor S1 and the acceleration sensor S2 can readily be detected. However, it is not required to rotate at the maximum speed at which the gantry rotating part 130 suddenly resonates, which may cause damages.

In Step C35, outputs of the acceleration sensors S1 and S2 are sensed at the sample time $T_1, T_2 \ldots T_n$.

In Step C36, when strong vibration, is sensed at the certain cycle by the acceleration sensors S1 and S2, it is determined immediately that it is in the condition of mechanical resonance. In a case of non mechanical resonance, it proceeds to Step C38 while in a case of mechanical resonance, it proceeds to Step C37.

In Step C37, in order to escape from the mechanical resonance, at least one of the self-propelled counter loads M1-M4 is moved by the certain distance. The certain distance is not a value obtained from the operation but a predetermined distance, e.g., 10 cm. After Step C37, it proceeds back to Step C35 to escape from the mechanical resonance.

In Step C38, as described in FIG. 4, the eccentric amount of the center of mass CM of the gantry rotating part 130 is calculated from the outputs of the acceleration sensors S1 and S2.

In Step C39, it is determined whether the eccentric amount of the center of mass CM is less than a threshold value. The threshold value is obtained by considering the maximum rotational speed of the gantry rotating part 130 during CT scan operation. If the eccentric amount of the center of mass CM is less than the threshold value, it proceeds to Step C42. If the eccentric amount of the center of mass CM is not less than the threshold value, it proceeds to Step C40.

In Step C40, it is determined whether the number of operation C for the travel amount of the self-propelled counter loads M1 and the travel amount of the self-propelled counter loads M4 are larger than the predetermined number P. If the number of operation C is larger than the predetermined number P, it proceeds to Step C44. If the number of operation C is not larger than the predetermined number P, it proceeds to Step C41.

In Step C41, the travel amount of each the self-propelled counter load M is calculated, and the self-propelled counter load M is moved by the travel amount obtained by the actuator controller 137. Theoretically, travel of the self-propelled counter load M1 and the self-propelled counter load M4 makes the eccentric amount of the center of mass CM less than the threshold value. Therefore, the operation may be finished but for confirmation, it proceeds to Step C35, and the outputs of the acceleration sensors S1 and S2 are sensed to confirm the actual rotational condition of the gantry rotating part 130.

In Step C42, the eccentric amount of the center of mass CM is less than the threshold value, the self-propelled counter load M1 through the self-propelled counter load M4 are locked. Concretely, the pole of the movable piece and the pole of the stator of the linear motor equipment, both facing to the other are set different.

In Step C43, the condition of the gantry rotating part 130 is transmitted to the operation console 50 for the image reproduction. The focus displacement of the X-ray tube 102 is important when the image is reproduced from the projection data. Therefore, even though the eccentric amount of the center of mass CM is less than the threshold value, the vibration condition obtained from the sensor is transmitted to the operation console 50, so that the image can be reproduced while the focus displacement of the X-ray tube 102 is taken into consideration.

In Step C44, since the number of operation C is larger than the predetermined number P, the rotation of the gantry rotating part 130 is stopped. Thereafter, the error log is transmitted to the operation console 50. Even through the self-propelled counter load M1 and the self-propelled counter load M4 are moved the predetermined times P, the eccentric amount of the center of mass CM of the gantry rotating part 130 cannot decrease. This is because the bearing 90 may be damaged or the components inside the gantry rotating part 130 may be damaged.

Second Embodiment

Figure 6:
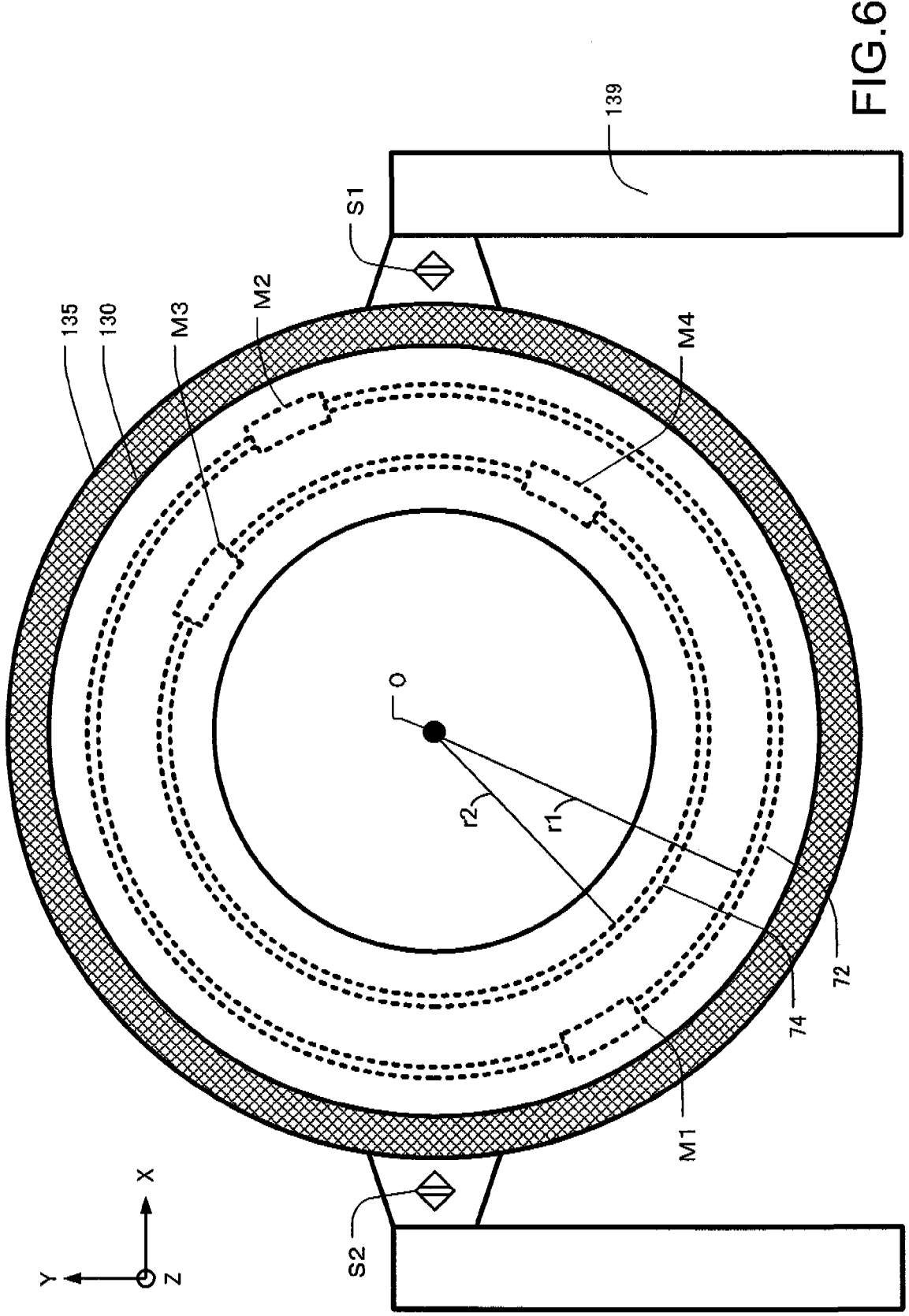
FIG. 6 is a schematic view showing the second embodiment of the gantry rotating part 130 of the X-ray CT apparatus 100 in X-Y plane.

FIG. 6 is a schematic view of the second embodiment showing the gantry rotating part 130 of the X-ray CT apparatus 100 in X-Y plane. The X-ray tube 102 and other components are not shown in FIG. 6. The circular ring rail 72 having a radius r1 and the circular ring rail 74 having a radius r2, the centers of which are the center of rotation O of the gantry rotating part 130 are attached to the gantry rotating part 130. Then, the self-propelled counter loads M1, M2 are attached along the ring rail 72. Further, the self-propelled counter loads M3, M4 are attached along the ring rail 74.

When the self-propelled counter loads M1-M4 have the same weight, one having a smaller radius can finely control. Therefore, there provided the circular ring rail 72 having the radius r1 and the circular ring rail 74 having the radius r2 different from the radius r1. In a case of large eccentric amount of the center of mass CM, the self-propelled counter loads M1 and M2 are moved, and in a case of small eccentric amount of the center of mass CM, the self-propelled counter loads M3 and M4 are moved, so that the eccentric amount of the center of mass CM is made less than the threshold value and readily and finely controlled.

Third Embodiment

Figure 7:
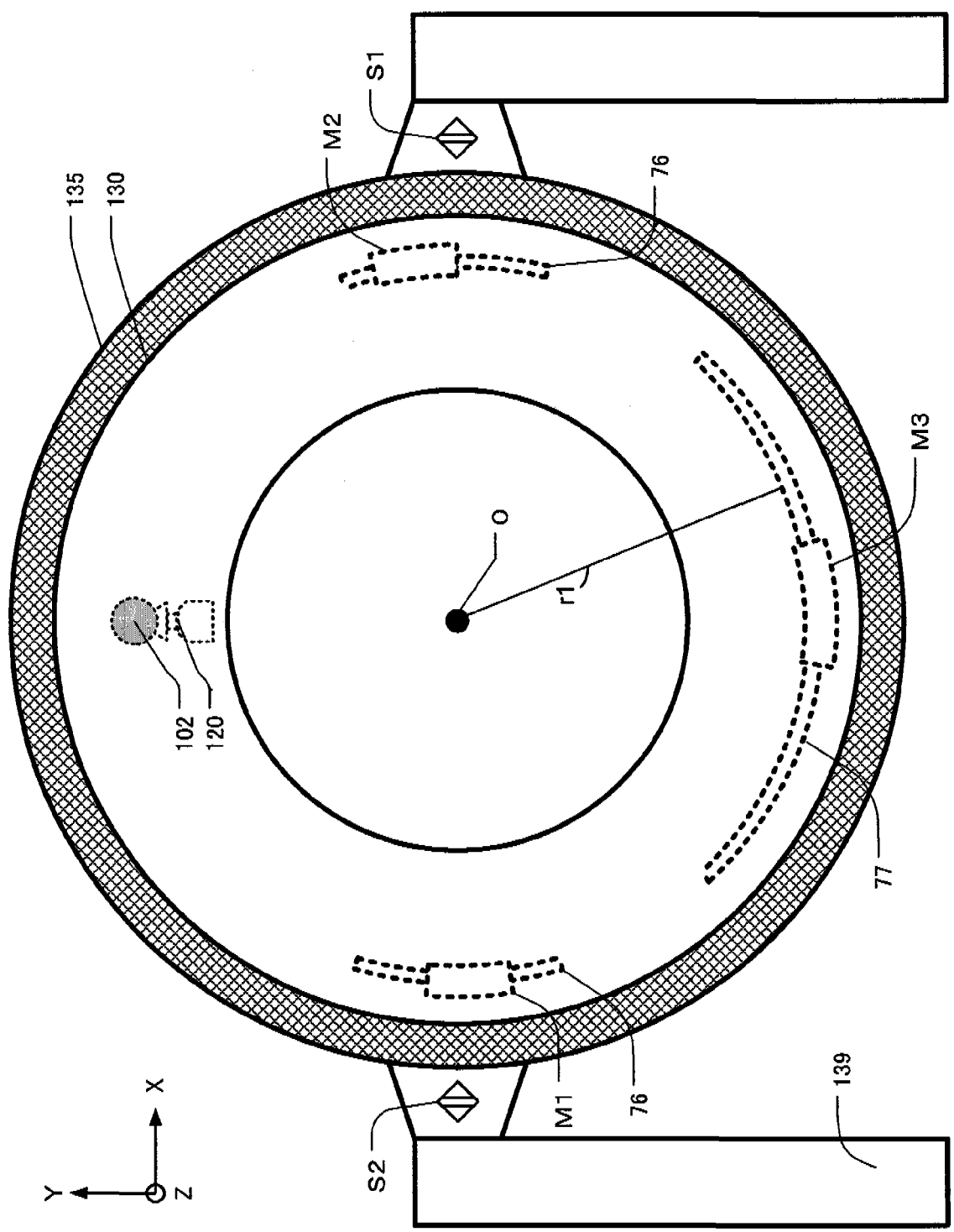
FIG. 7 is a schematic view showing the third embodiment of the gantry rotating part 130 of the X-ray CT apparatus 100 in X-Y plane.

FIG. 7 is a schematic view of the third embodiment showing the gantry rotating part 130 of the X-ray CT apparatus 100 in X-Y plane. Two circular arc ring rails 76 having a radius r1 and a circular arc ring rail 77 having a radius r1, the centers of which are the center of rotation O of the gantry rotating part 130 are attached to the gantry rotating part 130. Then, the self-propelled counter loads M1, M2 are attached along the ring rails 76. Further, the self-propelled counter loads M3, M4 are attached along the ring rail 77.

It is understood from FIG. 7 that the self-propelled counter load M3 has weight 1.5 to second times larger than the self-propelled counter load M1 or M2. Arc circular ring rails 76, 77 are used because if the center of mass CM is designed near the center of rotation O during designing, the self-propelled counter load M does not have to move by the long distance. Further, normally, since heavy weight acts on a portion on which the X-ray tube 102 and the collimator 120 are provided, the center of mass of the gantry rotating part 130 is eccentric to the X-ray tube 102. Accordingly, the center of mass CM of the self-propelled counter load 3 is placed near the center of rotation O. Furthermore, the self-propelled counter loads M1 and M2 have light weight compared to the self-propelled counter load M3, which readily and finely controlled.

The arc circular ring rail in third embodiment can be applied to the ring rails having different radiuses as in second embodiment. For example, the self-propelled counter loads M1 and M3 having the same weight, two arc circular ring rails 76 having a radius r2 shorter than the radius r1, and the ring rail 77 having a radius r1 are prepared. The self-propelled counter loads M2 and M3 are arranged at two ring rails 76 and the self-propelled counter load M1 is arranged at the ring rail 77 having the radius r1. Therefore, the self-propelled counter load M1 can be used for coarse adjustment and the self-propelled counter loads M2 and M3 can be used for fine adjustment.

The image reconstruction method of the present embodiments can be three-dimensional image reconstruction method with a conventionally well-known Feldkamp method. In the present embodiments, scanning is not limited to specific scanning method. In other words, conventional scanning (axial scanning), helical scanning, variable pitch helical scanning, helical shuttle canning can bring the same effects. Further, incline of the gantry 101 is not limited, that is, tilted gantry 101 what is called a tilt scanning, can bring the same effects. Furthermore, the present embodiments can be applied, e.g., to the heart beat image reconstruction synchronized with the heart beat signals.

In the present embodiments, the medical X-ray CT apparatus 100 has been described but the present embodiments can be applied to X-ray CT-PET apparatus, X-ray CT-SPECT apparatus and others utilized with the industrial X-ray CT apparatus or other apparatus.

What is claimed is:

1. A computed tomography apparatus comprising:
a rotating part having an X-ray tube and an X-ray detector for detecting X-rays from said X-ray tube;
at least two mass bodies provided at said rotating part, said at least two mass bodies comprising a first mass body and a second mass body, said first mass body movable in a direction of circumference of a first radius and said second mass body movable in a direction of circumference of a second radius different than said first radius;
a driving pad for moving at least one mass body of said at least two mass bodies;
a sensor for measuring vibration of said rotating part; and
a controller configured to control said driving part to move said at least one mass body based on outputs of said sensor.

2. A computed tomography apparatus according to claim 1, wherein when at least one of said X-ray tube and said X-ray detector is provided at said rotating part, a base position of said at least two mass bodies is determined.

3. A computed tomography apparatus according to claim 1, wherein said controller is configured to control said driving part to move said at least one mass body by a predetermined distance without calculating a travel amount of said at least one mass body, the controlling based on outputs of said sensor when said rotating part is in a condition of mechanical resonance.

4. A computed tomography apparatus according to claim 1, wherein said controller calculates a travel amount of said at least one mass body based on the outputs of said sensor, and said driving part is configured to drive said least one mass body the travel amount calculated by said controller.

5. A computed tomography apparatus according to claim 1 further comprising two supports for supporting said rotating part, said sensor including a first sensor configured to detect vibration in a first direction and a second sensor configured to detect vibration in a second direction perpendicular to said first direction, said first sensor and said second sensor being provided at said two supports, respectively.

6. A computed tomography apparatus according to claim 1, wherein said at least one mass body is moved as a movable piece of a linear motor equipment with respect to a stator.

7. A computed tomography apparatus according to claim 6, wherein said driving part comprises a plurality of coils arranged along the direction of circumference in which said at least one mass body is moved, and said at least one mass body comprises a magnet.

8. A computed tomography apparatus according to claim 1, wherein said at least two mass bodies have different weights.

9. A computed tomography apparatus according to claim 1, further comprising an image reconstruction device configured to reconstruct a tomographic image with a vibration condition of said rotating part transmitted from said sensor taken into consideration.

\* \* \* \* \*